US012569641B2

(12) United States Patent
Klinger

(10) Patent No.: US 12,569,641 B2
(45) Date of Patent: Mar. 10, 2026

(54) LEAKAGE VALVE AND VENTILATION TUBE SYSTEM

(71) Applicant: WILAmed GmbH, Kammerstein (DE)

(72) Inventor: Miriam Klinger, Schwabach (DE)

(73) Assignee: WILAMED GMBH, Kammerstein (DE)

( * ) Notice: Subject to any disclaimer, the term of this patent is extended or adjusted under 35 U.S.C. 154(b) by 1050 days.

(21) Appl. No.: 17/424,746

(22) PCT Filed: Jan. 24, 2019

(86) PCT No.: PCT/EP2019/051781
§ 371 (c)(1),
(2) Date: Jul. 21, 2021

(87) PCT Pub. No.: WO2020/151827
PCT Pub. Date: Jul. 30, 2020

(65) Prior Publication Data
US 2022/0105306 A1     Apr. 7, 2022

(51) Int. Cl.
*A61M 16/20*          (2006.01)
*A61M 16/08*          (2006.01)
(52) U.S. Cl.
CPC ...... *A61M 16/208* (2013.01); *A61M 16/0816* (2013.01); *A61M 2205/15* (2013.01); *A61M 2205/3337* (2013.01)
(58) Field of Classification Search
CPC ............ A61M 2205/15; A61M 16/208; A61M 16/20; A61M 16/209; A61M 16/0816;
(Continued)

(56) References Cited

U.S. PATENT DOCUMENTS 5,937,851 A     8/1999  Serowski et al.
6,112,745 A *  9/2000  Lang ........................ A62B 9/00
                                                    128/207.14
(Continued)

FOREIGN PATENT DOCUMENTS

DE          101 58 066 A1     6/2003
DE     10 2007 052 898 B3     4/2009
(Continued)

OTHER PUBLICATIONS

Japanese Office Action for Japanese Patent Application No. 2021-543319 dated Jul. 29, 2022, 4 pages.
(Continued)

*Primary Examiner* — Rachel T Sippel
*Assistant Examiner* — Gwynneth L Howell
(74) *Attorney, Agent, or Firm* — Merchant & Gould P.C.

(57)          ABSTRACT
A leakage valve in a patient ventilation system has a valve housing constructed from a first and second housing parts. The housing parts form a fluid channel with a circular cross-section. The valve housing has first and second connection pieces on the corresponding housing parts. A housing region between the connection pieces projects radially outward. An opening is at the height of the outwardly projecting housing region and enables fluid to pass as a leakage flow. A leakage channel for flow from the leakage valve circulates around part of the valve housing is formed by both housing parts. A catch mechanism includes catch lugs with an end-side detent follow the connection piece and axially engage an outer side of the connection piece. Wall regions between the catch lugs curve along and contact the connection piece inner surface. The housing parts rotate relative to one another in an engaged state.

13 Claims, 4 Drawing Sheets

(58) Field of Classification Search
     CPC .............. A61M 16/1095; A61M 16/08; A61M
                         16/0875; A61M 16/0825; A61M
                                                  2205/3337
     See application file for complete search history.

(56)                    References Cited

U.S. PATENT DOCUMENTS

| | | | |
|---|---|---|---|
| 7,174,893 B2* | 2/2007 | Walker | A61M 16/085 |
| | | | 128/205.24 |
| 9,744,323 B2* | 8/2017 | Hoftman | A61M 16/0434 |
| 2004/0035419 A1* | 2/2004 | Serowski | A61M 16/06 |
| | | | 128/202.27 |
| 2009/0114225 A1 | 5/2009 | Tappenhorn et al. | |
| 2015/0107588 A1* | 4/2015 | Cheung | A61M 16/026 |
| | | | 128/203.14 |

FOREIGN PATENT DOCUMENTS

| | | | |
|---|---|---|---|
| EP | 1 138 340 A2 | 10/2001 | |
| EP | 1 314 446 A2 | 5/2003 | |
| EP | 2 428 243 B1 | 10/2016 | |
| JP | 2018-510714 A | 4/2018 | |
| WO | 2016/063168 A1 | 4/2016 | |

OTHER PUBLICATIONS

International Search Report and Written Opinion of the International Searching Authority for International Patent Application No. PCT/EP2019/051781 mailed Oct. 23, 2019, 13 pages.

* cited by examiner

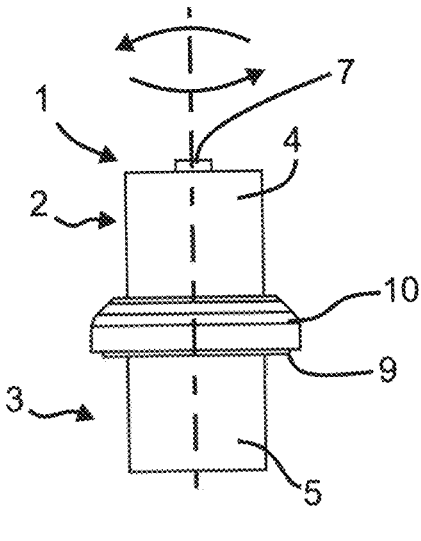
FIG. 7A
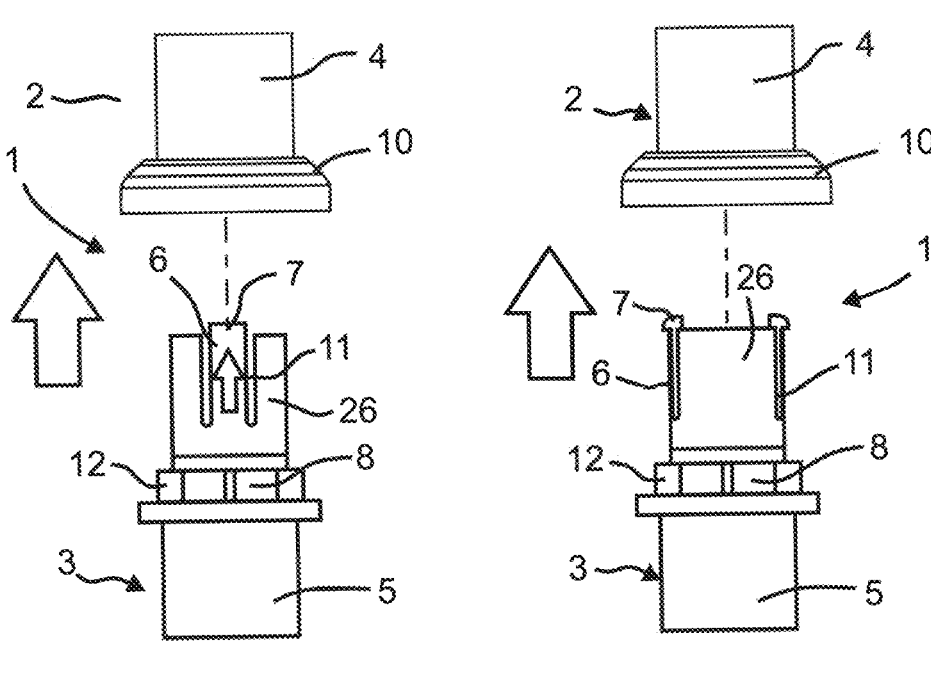
FIG. 7B                              FIG. 7C

LEAKAGE VALVE AND VENTILATION TUBE SYSTEM

This application is a National Stage Application of PCT/EP2019/051781, filed 24 Jan. 2019, and which application is incorporated herein by reference. To the extent appropriate, a claim of priority is made to the above-disclosed application.

The present invention relates to a leakage valve and to a ventilation tube system.

TECHNOLOGICAL BACKGROUND

Leakage valves are used for the so-called leakage ventilation. In this case, the patient to be ventilated receives a quantity of ventilation gas from a ventilator that is greater than the quantity of ventilation gas used by the patient during breathing. The remainder of this quantity of ventilation gas made available by the ventilator leaves the ventilation circuit via the leakage valve. During inspiration, the ventilation gas flows through the inner lumen of the leakage valve and at the same time washes all remainders of used air out of the leakage valve. The ventilator has a precisely defined delivery rate of ventilation gas. This delivery rate can be adjusted on the device side to the respective patient-dependent consumption rates (e.g., ventilation of an adult or an infant). Ventilators for leakage ventilation are usually precisely adjusted to the leakage quantity determined by the leakage valve. If there are fluctuations in the leakage quantity, they are not detected and therefore lead to an unwanted impairment of the ventilation, which is particularly important when ventilating newborns.

DOCUMENTED PRIOR ART

A leakage valve according to the preamble of claim 1 is known from EP 2 428 243 B1. The two housing parts have a mutual gradation and passage openings in the region of the housing region projecting radially outwards. In this known leakage valve, the two mutually engaged housing parts are supposed to be connected to one another by a clamp connection in order to avoid a rotation.

Furthermore, from U.S. Pat. No. 5,937,851, a leakage valve is known which also consists of an outer part and an inner part to be engaged therein. The inner part has spring lugs that engage the end-side end of the outer part. The outer part is spaced apart from the inner part to form a circulating gap-shaped baffle chamber and has three narrow elevations and one wide elevation on its broad front side, wherein the elevations together with the inner part allow, in regions, a leakage of $CO_2$-laden breathing air from the baffle chamber. In addition, a plurality of passage openings for an additional air passage from the inside of the leakage valve into the baffle chamber can be provided in the inner part at a distance from a housing region projecting radially outwards. The inner part and the outer part are supposed to be rotatable relative to one another. The problem with this design is that in the case of a mechanical impairment of the leakage valve, considerable fluctuations in the leakage quantity can occur.

From EP 1 314 446, a ventilation mask is known in which a mask main body is connected via a coupling element to an expiration element, wherein the coupling element, together with the expiration element, delimits a discharge channel. For this purpose, the expiration element is inserted in regions into a retaining connector of the coupling element. A maximum insertion depth is predefined by outer webs which run essentially parallel to a longitudinal axis of the expiration element along an outer side of the expiration element. Along its circumference, the expiration element also has a plurality of radially extending connection webs, between which discharge openings are provided. With their outer side, the connection webs run slightly inwards. The discharge openings are located above the outer webs. The expiration element is immobilized within the coupling element by locking elements which each engage in an associated recess from behind with a catch detent. A clearance between retaining piece and expiration element can support a simple rotatability of the expiration element within the retaining piece.

EP 1 138 340 A2 relates to a device for removal of at least partially used respiration gas from a respiration gas conduction system. The device comprises a first connector section and a second connector section as well as a removal device for removing a respiration gas partial flow, wherein the removal device is formed by at least one channel which is delimited at least partially by the wall of an elastomeric body. The channels are located in a region of a bulge projecting radially outwards. A rotary sleeve is provided for the rotatable coupling of the connection portions. In one specific embodiment, a plurality of radially resilient catch tongue elements can be provided which can be releasably engaged in a second connection element designed as a tube-like bushing.

DE 10 2007 052 898 B3 discloses a device for releasing breathing gas comprising an outer part and an inner part and having a cylindrical sliding surface. The inner part is rotatably attached within the outer part via a connection element. An annular discharge gap for breathing gas is formed between the connection element and the outer part. The discharge gap is formed by a spacing element between the connection element and the outer part. The spacing elements are designed such that the connection elements are secured against rotation with regard to the outer part. The spacing elements have snap-in pins that can be connected to the outer part.

From WO 2016/063168 A1, an adjustable leak valve is known which is configured to control a leak during respiratory therapy. The leak valve comprises a tubular body forming a flow path to conduct gas during respiratory therapy, wherein the tubular body has body orifices formed in the wall that communicate gas from the flow path through the wall. A sleeve is rotatable about the first axis with respect to the tubular body, wherein the sleeve essentially surrounds the body orifices in the body. In addition, the sleeve has sleeve orifices that are positionable such that they overlap with the body orifices. A tubular dial essentially surrounds the sleeve orifices in the sleeve, wherein the dial has a dial orifice formed therein. The dial opening is positionable to overlap with the sleeve orifices and the body orifices, wherein a rotational coupling between the tubular body, the sleeve, and the dial facilitates adjustable configuration of one or more properties of a leak pathway formed by positioning the overlapping of the dial orifice with at least one of the sleeve orifices and at least one of the body orifices to allow leak during respiratory therapy.

Problem Addressed by the Present Invention

The problem addressed by present invention is that of creating a leakage valve of the type in question, by means of which fluctuations in the leakage quantity can be effectively avoided.

Solution of the Problem

In contrast to the subject matter of EP 2 428 243 B1, the two housing parts of the leakage valve according to the invention can be rotated relative to one another in the engaged state. This has the advantage that no tensions can occur during use, since the two housing parts rotate relative to one another when mechanical impairments or torsional loads occur, so that no tensions leading to mechanical impairment can build up. This in turn has the effect that far fewer mechanical impairments, which lead to a fluctuation in the leakage quantity, can act on the leakage valve. In addition, the leakage valve according to the invention is characterized by a design that is favorable in terms of the production process.

The rotatability of the two housing parts relative to one another is expediently achieved by providing a gap clearance between the axially running catch lugs and the axially running inner wall of the first connection piece when the two housing parts are in the engaged state.

In the engaged state of the two housing parts, a gap clearance can also be provided between the end-side detent of the catch lugs and the end-side end of the first connection piece.

Furthermore, in the engaged state of the two housing parts, a gap clearance can be provided between the axially running outer wall of the curved wall regions and the axially running inner wall of the first connection piece.

The dimension of the gap (gap clearance) for the rotatability of the two housing parts is essentially 0.08 mm to 0.12 mm (i.e., 0.04 mm to 0.06 mm per side based on the diameter), preferably 0.09 mm to 0.11 mm (i.e., 0.045 mm to 0.055 mm per side based on the diameter).

The aforementioned design has the effect that the two housing parts can rotate relative to one another without the application of force, thereby avoiding the occurrence of mechanical stresses on the leakage valve during use, and the leakage quantity is not subject to any fluctuations.

The fact that a plurality of radially extending webs are provided along the perimeter of the second housing part, which delimit through openings, creates a particularly advantageous, extensive inflow region for the leakage flow into the leakage channel. At the same time, the design helps to facilitate the rotatability of the two housing parts relative to one another.

Except for the webs projecting radially outwards, the housing part having the through openings expediently has no gradation.

Since the webs project beyond the curved wall region towards the outside, it is possible to simultaneously use the webs as supports for the first housing part.

Expediently, there is a circulating annular space between the inner wall of the expanded housing region and the external end of the respective web. It is thus possible that ventilation gas can also flow around the end side of the web through the annular space located there and from there into the leakage channel to the outside, thus additionally stabilizing the leakage quantity.

In the engaged state of the two housing parts, the first housing part expediently rests, preferably in an abutting manner, on the webs of the second housing part. This design has the advantage that, by design, only very low surface friction occurs, which results in an excellent rotatability of the two housing parts relative to one another when the two housing parts are rotated relative to one another.

For this purpose, the first housing part expediently has a circulating step surface which, in the engaged state of the two housing parts, rests on the upper side of the webs.

The first and/or second housing part are preferably designed as one piece.

Furthermore, the second housing part can have an annular expansion or an annular projection in the region of the expanded housing region, which extends radially outwards and, together with the inner wall of the first housing part, forms the leakage channel leading into the open.

Since the annular expansion is provided with a circulating recess on its underside, the mechanical stability of the second housing part is additionally reinforced overall.

The present invention further relates to a ventilation tube system for use in leakage ventilation, wherein the ventilation tube system comprises a preferably heatable ventilation tube and a leakage valve.

The ventilation tube system is further characterized in that a connection sleeve for connecting the ventilation tube to the leakage valve and/or to a functional part is provided on at least one end, preferably on both ends of the ventilation tube.

The leakage valve is expediently located between the connection sleeve and a ventilation aid positioned on the patient.

The leakage valve is expediently located between the connection sleeve and a connector having probe connection means.

DESCRIPTION OF THE INVENTION USING EMBODIMENTS

In the following, an expedient embodiment of the leakage valve according to the invention will be described in detail. For the sake of clarity, recurring features are only denoted once. In the drawings:

FIG. 7 shows a depiction of the function or the assembly of the leakage valve according to the invention of FIG. 2 in the engaged state (FIG. 7a), in an exploded view (FIG. 7b), and also in an exploded view but rotated by 90° with regard to FIG. 7B (FIG. 7c).

Figure 1:
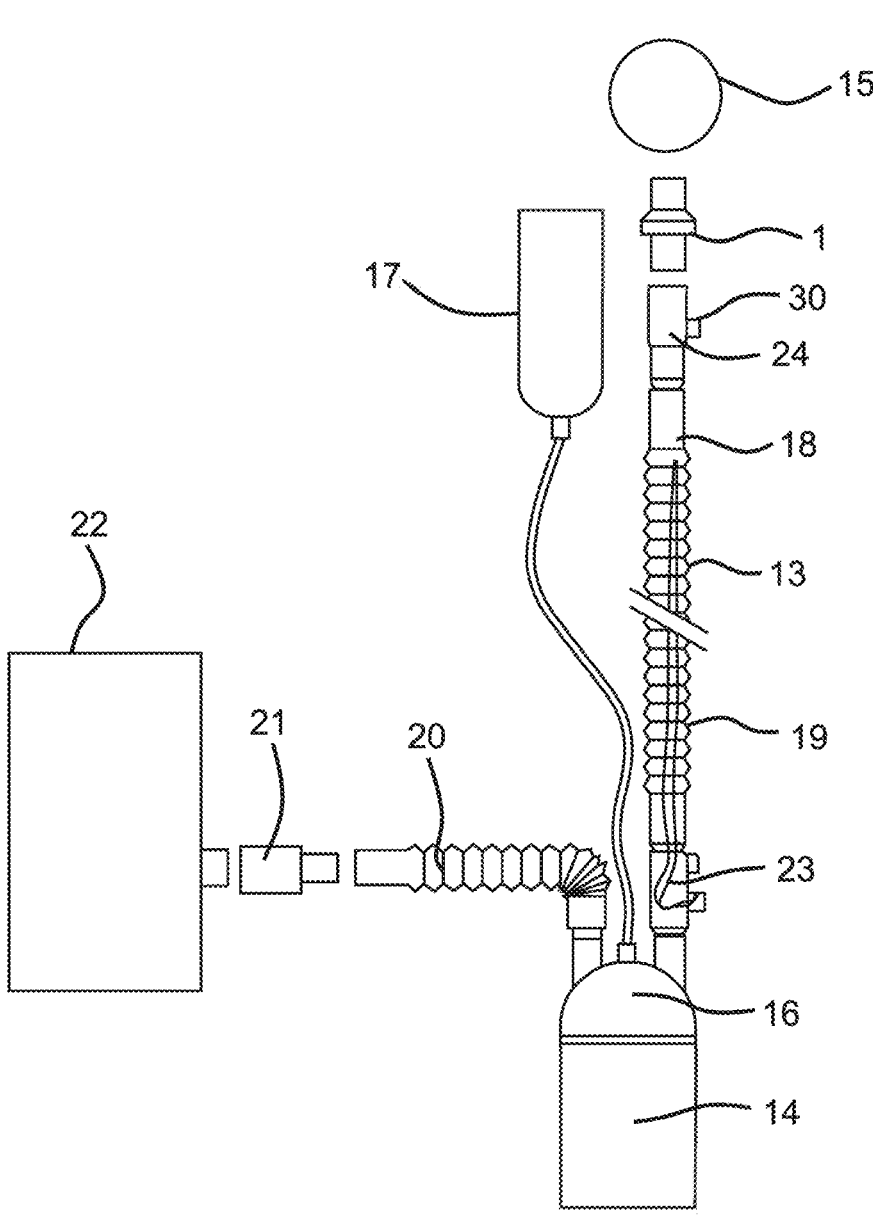
FIG. 1 shows a greatly simplified schematic depiction of a ventilation system for leakage ventilation.

FIG. 1 shows an example of an arrangement for leakage ventilation. Reference sign 15 denotes a ventilation device located on the patient, e.g., a ventilation mask which is provided with a connection piece (not depicted) and connected to a leakage valve 1 according to the invention. The leakage valve 1 can be followed, e.g., by a connector 24 having a connection for a probe.

Furthermore, a ventilation tube 13 is provided which, if necessary, can contain a heating wire provided to keep the ventilation gas within the ventilation tube at a specific temperature. However, a heating wire does not necessarily have to be present. The ventilation tube 13 has a connection sleeve 18, 19 at each end. Furthermore, the ventilation tube 13 is connected to a humidification chamber 16 of an air humidifier 14 via a further connector 23 having a connection for a probe. Specially conditioned ventilation gas is kept available in the humidification chamber 16. The humidification chamber 16 is connected to a fan 22 via a connecting tube 20 and a connector 21. In order to ensure a specific moisture content of the ventilation gas located within the humidification chamber 16, it is connected to a water reservoir 17. For ventilation, the conditioned ventilation gas stored in the humidification chamber 16 is, due to the overpressure generated by the fan 22, thus conveyed to the patient via the ventilation tube 13. The ventilation gas is inhaled by the patient and exhaled again via the ventilation mask. In this case, the patient is supplied with a quantity of ventilation gas that is greater than the quantity used by the patient during breathing. The remainder of the ventilation gas quantity made available by the ventilation gas leaves the ventilation circuit via the leakage valve 1. During inspiration, the ventilation gas flows through the inner lumen of the leakage valve and at the same time washes all remainders of used air out of the leakage valve.

During handling, it can frequently occur that the ventilation tube 13 to the ventilation device located on the patient, e.g., a ventilation mask, rotates, resulting in torsional forces acting on the leakage valve 1.

Figure 2:
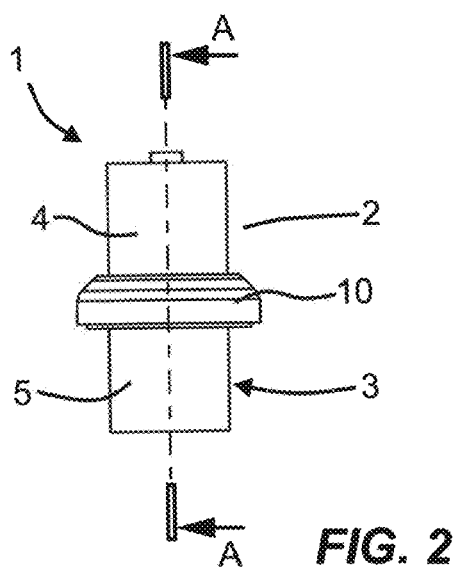
FIG. 2 is a side view of an expedient embodiment of a leakage valve according to the invention.

FIG. 2 shows one embodiment of a leakage valve according to the invention. The leakage valve 1 comprises a first round housing part 2 and a second round housing part 3, wherein a first connection piece 4 is provided on the first housing part 2 and a second connection piece 5 is provided on the second housing part 3. The leakage valve 1 is connected to the ventilation device 15, e.g., a ventilation mask, by means of the connection piece 4. The second connection piece 5 is used to connect the leakage valve 1 to the connector 24 having probe connection means 30 or directly to the ventilation tube 13. Approximately in the central region of the leakage valve 1 is an expanding housing region 10 in which a circulating narrow leakage channel 9, cf. FIG. 2, is located for the leakage flow to exit from the leakage valve 1 into the open.

Figure 3:
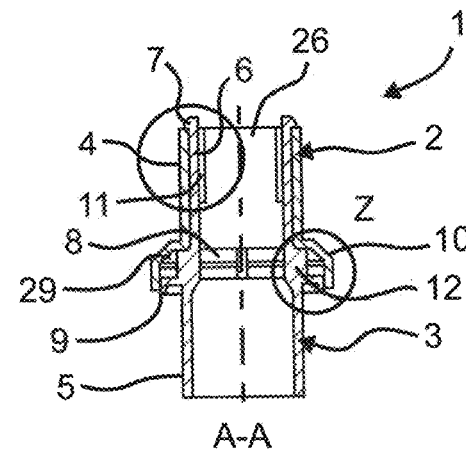
FIG. 3 is a sectional view of the leakage valve according to FIG. 2 along the section line A-A.

FIG. 3 shows the structural design of the leakage valve 1. The second housing part 3 forms the inner lumen of the leakage valve 1, wherein the first housing part 2 is arranged on the outside of the second housing part 3 and engaged in the axial direction via a snap connection. For this purpose, the first housing part 2 is pushed over the cylindrical region of the second housing part 3. The cylindrical region has curved wall regions 26, between which slots 11 are provided. These slots 11 form catch lugs 6 with detents 7 on the upper side which engage with the upper end side of the first housing part 2 and thus immobilize the latter in an axial holding position. Between the inner wall of the first housing part 2 and the outer side of the second housing part 3, the narrow leakage channel 9, through which ventilation gas can reach the open, is provided in the region of the expanding housing region 10.

Furthermore, on the second housing part 3, webs 12 facing radially outwards are provided along the circumference of the second housing part 3, which delimit through openings 8. Ventilation gas can pass via the through openings 8 from the inner lumen of the leakage valve into the interior of the expanded region 10 and from there into the circulating leakage channel 9. The through openings 8 are extensive because they are only delimited by the radially running webs 12.

In the bottom region of the webs 12, an annular expansion 27 is provided, the end face of which on the outer circumference, together with the inner wall of the first housing part 2, forms the leakage channel 9 in the region of the housing expansion 10.

The first housing part 2 has a preferably circulating step surface 25 which, in the engaged state of the two housing parts 2, 3, rests on the upper side of the webs 12.

Figure 4:
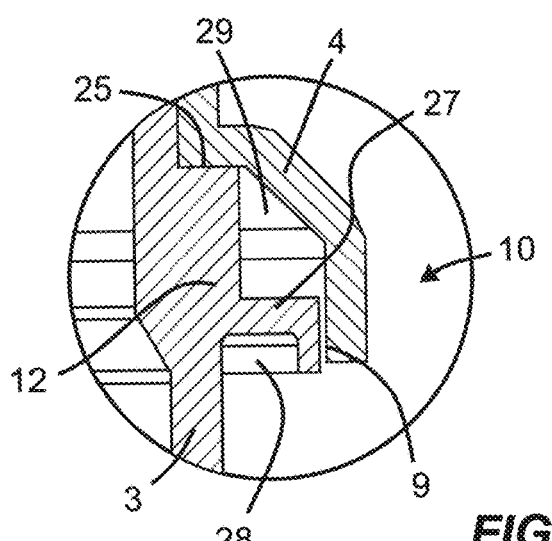
FIG. 4 is a detailed sectional view in region Z of FIG. 3.
Figure 4A:
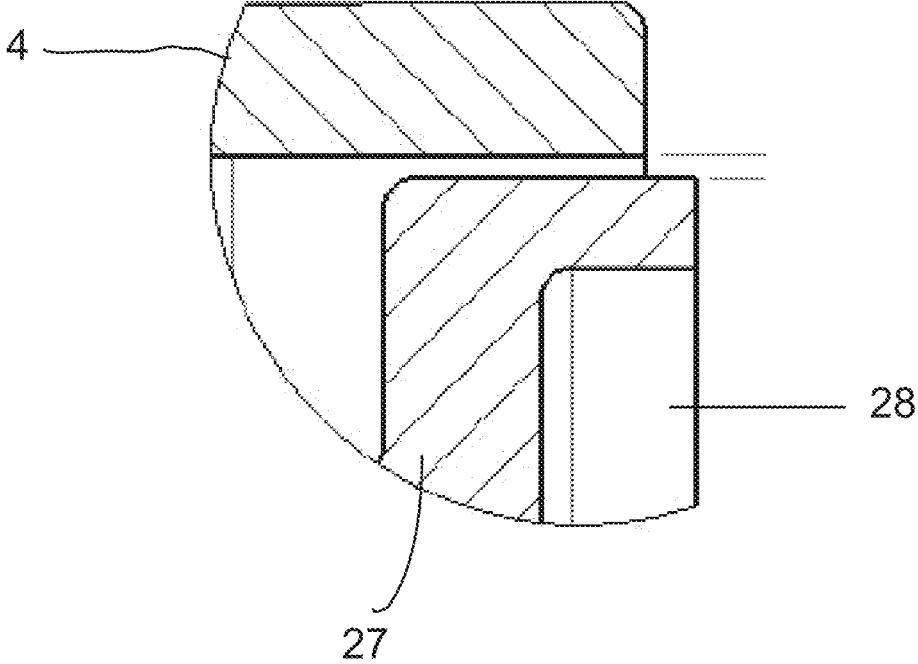
FIG. 4A is an enlarged detail sectional view of a portion of FIG. 4.

The concept can be seen somewhat more clearly in FIG. 4 and FIG. 4A. The annular expansion 27 has a circulating recess 28 on its underside, which results in a mechanical stiffening of the second housing part 3 or the annular expansion 27. This mechanical stability prevents the leakage channel 9 from changing under mechanical stress, resulting in an impairment of the leakage flow.

Figure 3A:
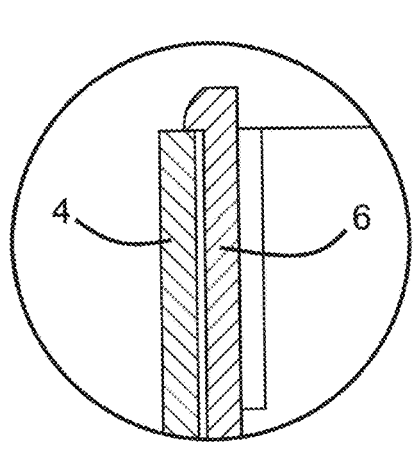
Figure 3A:
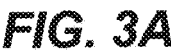

The rotatability of the two housing parts 2, 3 relative to one another in the engaged state, which can be carried out without exertion of force, is achieved in that a slight gap clearance is provided between the axially running outer wall of the first housing part 2 in the region of the catch lugs 6 and the inner wall of the first connection piece 4. A corresponding gap clearance, shown in FIG. 3A can also be provided between the end-side detent 7 of the catch lugs 6 and the end-side end of the first connection piece 4. A slight gap clearance can also be provided between the axially running outer wall, the curved wall regions 26 of the first housing part 2, and the axially running inner wall of the first connection piece 4.

The dimension of the gap (gap clearance) for the rotatability of the two housing parts is essentially 0.08 mm to 0.12 mm (i.e., 0.04 mm to 0.06 mm per side based on the diameter), preferably 0.09 mm to 0.11 mm (i.e., 0.045 mm to 0.055 mm per side based on the diameter). For example, the gap clearance in relation to the diameter is 0.10 mm, i.e., 0.05 mm per side.

Figure 5:
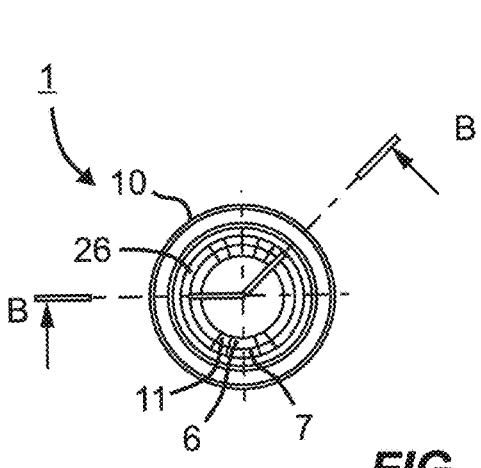
FIG. 5 is a plan view of the upper side of the leakage valve according to FIG. 2.

FIG. 5 is a plan view of the leakage valve 1. It shows the two opposite catch lugs 6 having the end-side detents 7 on the upper side of the first housing part 2, which overlap the end on the upper side of the second housing part 3.

Figure 6:
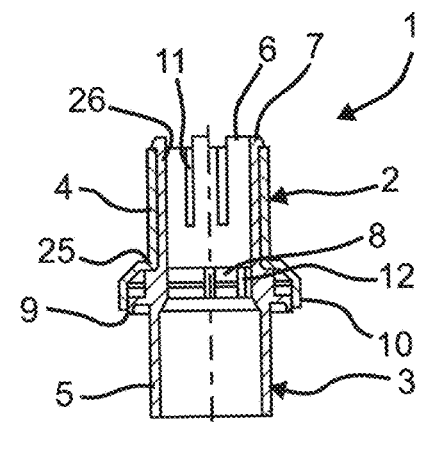
FIG. 6 is a sectional view along the angled intersections B-B of FIG. 5.

As is clear from FIG. 6, the upper side region of the first housing part 2, i.e., the curved wall region 26, is designed to be smooth, i.e., without a step, up to the upper side of the webs 12. The same applies to the corresponding region of the first housing part 2 which is arranged on the outside and forms the first connection piece 4.

As can be seen from FIG. 7a, the two housing parts 2 and 3 of the leakage valve 1 according to the invention can be rotated relative to one another very easily in the engaged state. Thus, no torsional forces can build up on the housing of the leakage valve 1 if, e.g., the ventilation tube 13 is rotated.

FIGS. 7b and 7c are exploded views of the leakage valve. The respective region of the through openings 8 provided along the circumference, through which breathing gas can pass from the inner lumen of the leakage valve 1 into the annular space 29 and from there into the annular leakage channel 9 (cf. e.g., FIG. 3), is clearly visible.

The design according to the invention also makes it possible to produce the housing parts 2 and 3 in a simple manner in one piece from plastic in an injection molding process.

It must expressly be noted that sub-combinations of the described feature complexes and embodiments are also regarded as expressly included in the subject matter of the present invention.

LIST OF REFERENCE SIGNS

1 Leakage valve
2 First housing part
3 Second housing part
4 First connection piece
5 Second connection piece
6 Catch lug
7 Detent 8 Through opening
9 Leakage channel
10 Expanded housing region
11 Slot
12 Web
13 Ventilation tube
14 Humidifier
15 Ventilation device
16 Humidification chamber
17 Water reservoir
18 Connection sleeve
19 Connection sleeve
20 Connecting tube
21 Connector
22 Fan
23 Connector having probe connection means
24 Connector having probe connection means
25 Step surface
26 Curved wall region
27 Annular expansion
28 Recess
29 Annular space

The invention claimed is:

1. A leakage valve for a patient ventilation system comprising:

a valve housing constructed from a first housing part and a second housing part, wherein the housing parts form a fluid channel with a circular cross section, wherein the valve housing comprises the following:

a housing region projecting radially outward;

a first connection piece on the first housing part having an outer face end opposite to the housing region;

a second connection piece on the second housing part, wherein said housing region is arranged between the first and second connection pieces;

through openings arranged in the second housing part are covered by the housing region and the through openings enable fluid to pass out of the fluid channel as a leakage flow;

a leakage channel for outlet of the leakage flow out of the leakage valve, which is arranged approximately at the height of the housing region, circulating at least around a part, of the valve housing, and formed by the first and second housing parts;

a catch mechanism, by which the first and second housing parts are connectable to one another, wherein at least one catch lug with an end-side detent and curved according to an inner radius of the first connection piece are provided as a catch mechanism, which extend along the first connection piece in contact with an inner side in an engaged state, engage on said outer face end of the first connection piece by the end-side detent and guarantee an axial engagement, and wall regions are provided between the catch lugs, which are curved according to the inner radius of the first connection piece, and which are in contact with the inner surface of the first connection piece, wherein the first and second housing parts rotatable relative to one another in the engaged state, a plurality of webs extending radially outward are provided on the second housing part along the circumference, and said through openings are provided between the webs, the webs project beyond the wall regions towards outside, and a circulating annular space is between the inner wall of the housing region and an outer end of a respective one of the webs.

2. The leakage valve according to claim 1, wherein in the engaged state of the first and second housing parts, a gap clearance is provided between an axially extending outer wall of the catch lugs and an axially running inner wall of the first connection piece.

3. The leakage valve according to claim 1, wherein, in the engaged state of the first and second housing parts, a gap clearance is provided between the end-side detent of the catch lugs and an end-side end of the first connection piece.

4. The leakage valve according to claim 1, wherein, in the engaged state of the first and second housing parts, a gap clearance is provided between an axially extending outer wall of the wall regions and an axially running inner wall of the first connection piece.

5. The leakage valve according to claim 1, wherein in the engaged state of the first and second housing parts, the first housing part rests on the webs.

6. The leakage valve according to claim 1, wherein the first housing part has a circulating step surface which rests on an upper side of the webs in the engaged state of the first and second housing parts.

7. The leakage valve according to claim 1, wherein the second housing part has an annular expansion proximate the housing region.

8. The leakage valve according to claim 7, comprising a circulating recess radially inward from the annular expansion.

9. Ventilation tube system for use in leakage ventilation, comprising ventilation tube and a leakage valve according to claim 1.

10. The ventilation tube system according to claim 9, wherein a connection sleeve for connecting the ventilation tube to the leakage valve is provided on at least one end of the ventilation tube.

11. The ventilation tube system according to claim 10, wherein the leakage valve is located between the connection sleeve and a ventilation device positioned on a patient.

12. The ventilation tube system according to claim 10, wherein the leakage valve is followed by the connection sleeve and a connector having probe connectors.

13. The ventilation tube system according to claim 9, wherein the ventilation tube is heated.

* * * * *